United States Patent
Song

(10) Patent No.: US 9,962,140 B2
(45) Date of Patent: May 8, 2018

(54) ULTRASOUND PROBE AND METHOD OF CONTROLLING THE SAME

(71) Applicant: SAMSUNG MEDISON CO., LTD., Gangwon-Do (KR)

(72) Inventor: In Seong Song, Daegu (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 512 days.

(21) Appl. No.: 14/792,273

(22) Filed: Jul. 6, 2015

(65) Prior Publication Data

US 2016/0135785 A1 May 19, 2016

(30) Foreign Application Priority Data

Nov. 13, 2014 (KR) .................. 10-2014-0157962

(51) Int. Cl.
*A61B 8/00* (2006.01)
*A61B 8/08* (2006.01)
*A61B 8/14* (2006.01)

(52) U.S. Cl.
CPC .............. *A61B 8/4461* (2013.01); *A61B 8/14* (2013.01); *A61B 8/466* (2013.01); *A61B 8/483* (2013.01); *A61B 8/5269* (2013.01); *A61B 8/54* (2013.01)

(58) Field of Classification Search
CPC ........... A61B 8/4461; A61B 8/14; A61B 8/54; A61B 8/5269; A61B 8/483; A61B 8/466
See application file for complete search history.

(56) References Cited

U.S. PATENT DOCUMENTS

| | | | |
|---|---|---|---|
| 2005/0090740 A1 | 4/2005 | Raitzer et al. | |
| 2005/0124887 A1 | 6/2005 | Li | |
| 2006/0241424 A1* | 10/2006 | Akiyama | A61B 8/00 600/437 |
| 2009/0264767 A1 | 10/2009 | Griffin et al. | |
| 2010/0156404 A1 | 6/2010 | Han et al. | |
| 2011/0071398 A1 | 3/2011 | Hwang et al. | |
| 2012/0065517 A1* | 3/2012 | Goodnow | A61B 8/12 600/467 |

FOREIGN PATENT DOCUMENTS

| | | |
|---|---|---|
| GB | 2 067 759 A | 7/1981 |
| GB | 2 216 660 A | 10/1989 |

OTHER PUBLICATIONS

European Communication under Rule 71(3) EPC, issued in corresponding European Patent Application No. 15 175 279.7, dated Jul. 18, 2017.
Extended European Search Report issued in corresponding European Patent Application No. 15175279.7, dated Apr. 20, 2016.

\* cited by examiner

*Primary Examiner* — Peter Luong
(74) *Attorney, Agent, or Firm* — McDermott Will & Emery LLP

(57) ABSTRACT

Disclosed herein are an ultrasound probe and a method of controlling the same. Image quality reduction in a 3D image may be prevented, and blurring of an ultrasound image may be removed via image correction by independently installing position detecting sensors on a transducer module and a motor of the ultrasound probe, detecting a backlash increasing as time, and compensating a variation of the backlash.

The ultrasound probe includes a first sensor to detect a position of a transducer changed by rotation, a second sensor to detect rotation of a driving device, and a controlling to determine a backlash between signals of the first and second sensors and correcting an ultrasound image.

16 Claims, 15 Drawing Sheets

(a) BLURRING OF IMAGE BEFORE IMAGE CORRECTION (b) IMAGE FROM WHICH BLURRING IS REMOVED AFTER IMAGE CORRECTION (c) IMAGE BLURRING CAUSED BY BACKLASH (a)

(b)

ULTRASOUND PROBE AND METHOD OF CONTROLLING THE SAME

CROSS-REFERENCE TO RELATED APPLICATION(S)

This application claims the benefit of Korean Patent Application No. 10-2014-0157962, filed on Nov. 13, 2014 in the Korean Intellectual Property Office, the disclosure of which is incorporated herein by reference.

BACKGROUND

1. Field

Embodiments of the present disclosure relate to ultrasound probes emitting ultrasound to an object and receiving echo ultrasound reflected by the object, and methods of controlling the same.

2. Description of the Related Art

Ultrasound diagnostic apparatuses non-invasively generate an image of a target region inside an object such as a soft tissue tomogram or a blood stream tomogram by irradiating ultrasonic signals generated by transducers of a probe toward the target region from the surface of the object and receiving reflected ultrasonic signals (ultrasonic echo signals). Thus, the ultrasound diagnostic apparatuses have been used for medical purposes, for example, to examine the inside of the object, detect impurities, and measure injury.

Since ultrasound diagnostic apparatuses are small and inexpensive, display an image in real time, and provide high safety without causing X-ray exposure, as compared to other diagnostic imaging apparatuses, such as X-ray diagnosis apparatuses, computed tomography (CT) scanners, magnetic resonance imaging (MRI) apparatuses, and nuclear medicine diagnosis apparatuses, the ultrasound diagnostic apparatuses have been widely used with other diagnostic imaging apparatuses.

Particularly, a three-dimensional (3D) ultrasound imaging apparatus generates a 3D ultrasound image and visualizes the generated 3D image on a display apparatus by acquiring 3D data of an object by using a probe, or the like, and volume-rendering the acquired 3D data.

In order to realize an image by using an ultrasound diagnostic apparatus, a unit and/or device that perform interconversion between ultrasound signals and electric signals are required. In this regard, the unit and/or device are referred to as an ultrasound probe or ultrasound transducer.

In general, an ultrasound probe includes an ultrasound module including a piezoelectric layer to perform interconversion between electric signals and sound signals while a piezoelectric material vibrates, a matching layer to reduce a difference in acoustic impedance between the piezoelectric layer and a human body thereby efficiently transferring ultrasound generated by the piezoelectric layer to a target region of the human body, a lens layer to focus ultrasound proceeding forward from the piezoelectric layer to a predetermined point, a backing layer to block transmission of the ultrasound proceeding backward from the piezoelectric layer thereby preventing image distortion. Most medical ultrasound probes commonly used in the art include a plurality of ultrasound devices, except or medical ultrasound probes for special use including a single ultrasound device.

Such medical ultrasound probes are classified according to various standards such as number of ultrasound devices, alignment type of ultrasound devices, shape of alignment axis ultrasound devices, or applications thereof. The medical ultrasound probes may be classified into a single device-type ultrasound probe and a multi device-type ultrasound probe based on the number of ultrasound devices. In this regard, the multi device-type ultrasound probes may be classified into one-dimensional (1D) array-type ultrasound probes in which ultrasound devices are arranged in one axis and two-dimensional (2D) array-type ultrasound probes in which ultrasound devices are arranged in a plurality of axes to cross each other, based on the alignment type of ultrasound devices.

In recent years, an ultrasound probe capable of realizing a 3D image, particularly, a 3D dynamic image, of the inside of the human body has been required. 3D images may be realized by using an ultrasound diagnostic apparatus by rotating a transducer in addition to using conventional 1D array-type and 2D array-type ultrasound probes.

Conventionally, when a 3D image is generated based on signals from a sensor acquired while an ultrasound device of an ultrasound probe wobbles, there is no separate mechanical device for compensating errors. Accordingly, as a rotation angle of a motor changes with time, a backlash is caused after a predetermined delay. The backlash is a change in a swing angle of a swing motion, in which an alignment axis of an ultrasound device moves in a predetermined angle. The backlash is a delay occurring when a rotational motion of a motor is transferred to an alignment axis of an ultrasound transmitting and receiving device.

In this regard, blurring of an ultrasound image occurs in some regions due to the backlash of a clockwise CW image received in the clockwise direction of the ultrasound probe and a counter clockwise CCW image received in the counter clockwise direction thereof.

SUMMARY

Therefore, it is an aspect of the present disclosure to provide an ultrasound probe and a method of controlling the same, by which image quality reduction in a 3D image is prevented, and blurring of an ultrasound image is removed via image correction by independently installing position detecting sensors on a module and a motor of the ultrasound probe, detecting a backlash increasing as time, and compensating a variation of the backlash.

Additional aspects of the disclosure will be set forth in part in the description which follows and, in part, will be obvious from the description, or may be learned by practice of the disclosure.

In accordance with one aspect of the present disclosure, an ultrasound probe including a first sensor configured to detect a position of the transducer changed by rotation, a second sensor configured to detect rotation of the driving device, and a controller configured to determine a backlash value between a signal of the first sensor and a signal of the second sensor and correct an ultrasound image.

The driving device may include a driving motor configured to generate a rotational force to rotate the transducer, and a driving shaft configured to transfer the rotational force of the driving motor to the transducer.

The first sensor and the second sensor may be installed in the ultrasound probe.

The controller may calculate a time difference variation between a signal of the first sensor and a signal of the second sensor and determine the backlash value by using the calculated time difference variation.

The controller may calculate a time difference between a signal of the first sensor and a signal of the second sensor when the transducer rotates clockwise or counter clockwise.

The controller may determine the backlash value by using a variation based on the detected time difference between the signal of the first sensor and the signal of the second sensor and an initial time difference.

The controller may correct a rendered clockwise image and a rendered counter clockwise image by using the determined backlash value when a rendered ultrasound image is generated.

The controller may shift the clockwise image and the counter clockwise image by the calculated backlash value of the clockwise direction and the counter clockwise direction with respect to a central axis of the transducer.

In accordance with another aspect of the present disclosure, a method of controlling an ultrasound probe includes determining a backlash value between a signal of a first sensor and a signal of a second sensor installed in the ultrasound probe; and correcting an ultrasound image by using the determined backlash value.

The signal of the first sensor may be a signal output as a result of detecting a position of the transducer changed by rotation.

The signal of the second sensor may be a signal output as a result of detecting rotation of the driving device.

The determining of the backlash value between the signal of the first sensor and the signal of the second sensor may be performed by calculating a time difference variation between the signal of the first sensor and the signal of the second sensor, and determining the backlash value by using the calculated time difference variation.

The calculating of the time difference between the signal of the first sensor and the signal of the second sensor may be performed by calculating a time difference between the signal of the first sensor and the signal of the second sensor when the transducer rotates clockwise or counter clockwise.

The determining of the backlash value may be performed by using a variation based on the detected time difference between the signal of the first sensor and the signal of the second sensor and an initial time difference.

The correcting of the ultrasound image may be performed by correcting a rendered clockwise image and a rendered counter clockwise image by using the determined backlash value when a rendered ultrasound image is generated.

The correcting of the ultrasound image may be performed by shifting the clockwise image and the counter clockwise image by the calculated backlash value of the clockwise direction and the counter clockwise direction with respect to a central axis of the transducer.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
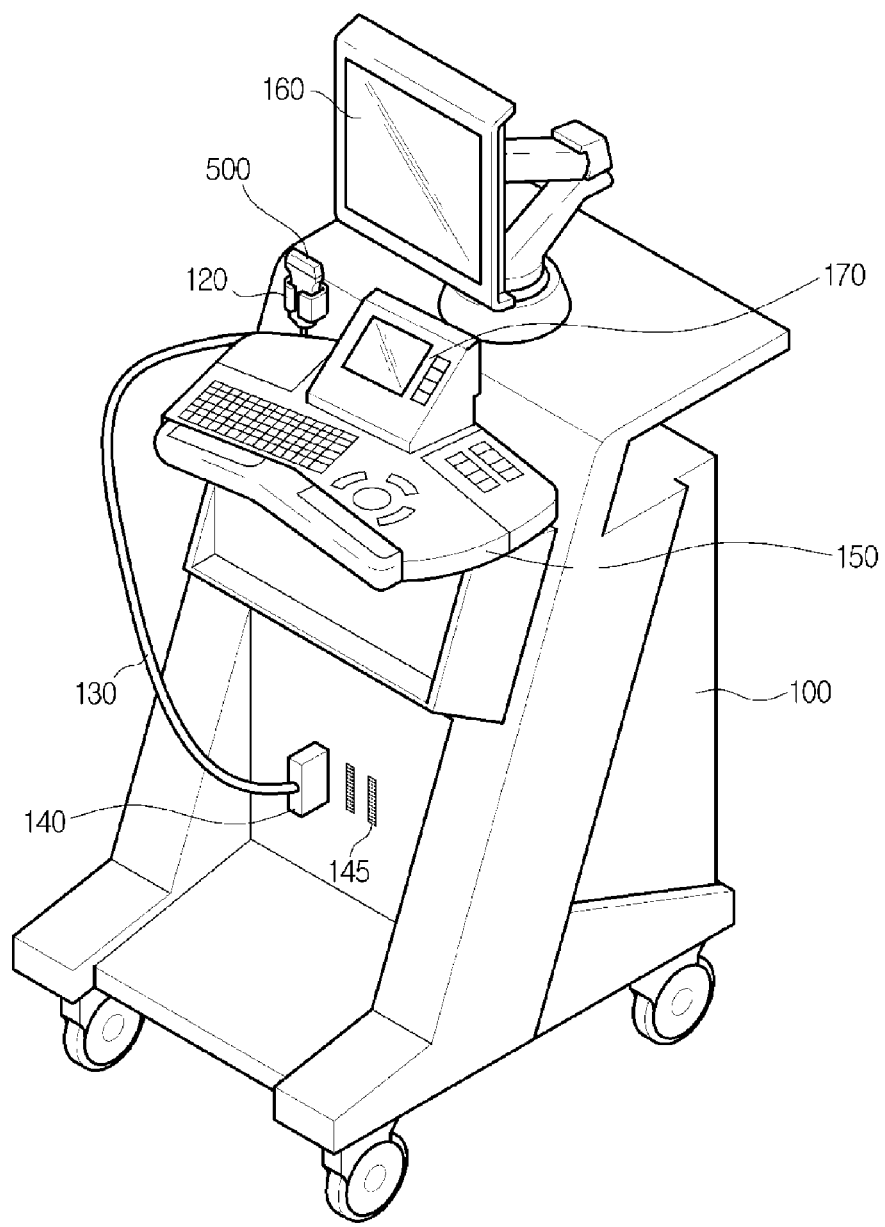
FIG. 1 is a perspective view illustrating an ultrasound imaging apparatus according to an exemplary embodiment.

Reference will now be made in detail to the embodiments of the present disclosure, examples of which are illustrated in the accompanying drawings, wherein like reference numerals refer to like elements throughout.

Hereinafter, an ultrasound probe and a method of controlling the same will be described in detail with reference to the drawings.

A medical imaging apparatus according to an exemplary embodiment may refer to an X-ray imaging apparatus, a fluoroscopic X-ray system, a computed tomography (CT) scanner, a magnetic resonance imaging (MRI) apparatus, a positron emission tomography apparatus, and an ultrasound diagnostic apparatus. Hereinafter, an ultrasound imaging apparatus will be described as a medical imaging apparatus by way of example. As used herein, the term 'ultrasound image' refers to an image of an object acquired using ultrasound. As used herein, the term object" refers to human, animal, metal, non-metal, or a part thereof. For example, the object may include organs such as liver, heart, uterus, brain, breast, and abdomen or blood vessels. In addition, the object may also include phantom. Phantom refers to a material that has density, effective atomic number, and volume similar to biological tissues.

As used herein, the term "user" refers to medical professionals such as doctors, nurses, medical laboratory technologists, medical imaging professionals, ultrasound examiners, medical equipment technicians, and the like, without being limited thereto.

FIG. 1 is a perspective view illustrating an ultrasound imaging apparatus according to an exemplary embodiment. Referring to FIG. 1, the ultrasound imaging apparatus includes a main body 100, an ultrasound probe 500, an input unit 150, and a display 160.

The main body 100 may be provided with at least one female connector 145 at one side thereof. A male connector 140 connected to a cable 130 may be physically coupled to the female connector 145.

Meanwhile, a plurality of casters (not shown) may be provided at the bottom of the main body 100 to allow the ultrasound imaging apparatus to move. The plurality of casters may fix the ultrasound imaging apparatus at a predetermined place or allow the ultrasound imaging apparatus to move in a predetermined direction. Such ultrasound imaging apparatuses are referred to as cart-type ultrasound imaging apparatuses.

Alternatively, the ultrasound imaging apparatus may be a portable ultrasound imaging apparatus that may be carried during a long distance traveling different from that illustrated in FIG. 1. In this regard, the portable ultrasound imaging apparatus may not be provided with casters. Examples of the portable ultrasound imaging apparatus may include a picture archiving and communication system (PACS) viewer, a smart phone, a laptop computer, a personal digital assistant (PDA), and a tablet PC, without being limited thereto.

The ultrasound probe 500 that contacts the surface of the body of an object may transmit and receive ultrasonic signals. Particularly, the ultrasound probe 500 may transmit ultrasound into the object in accordance with a transmit signal received from the main body 100, receive echo ultrasound reflected by a specific region inside the object, and transmit the received echo ultrasound to the main body 100.

One end of the cable 130 may be connected to the ultrasound probe 500, and the other end of the cable 130 may be connected to the male connector 140. The male connector 140 connected to the other end of the cable 130 may be physically coupled to the female connector 145 of the main body 100.

Alternatively, differently from FIG. 1, the ultrasound probe 500 may be wirelessly connected to the main body 100. In this case, the ultrasound probe 500 may transmit the echo ultrasound received from the object to the main body 100 in a wireless manner. In addition, a plurality of ultrasound probes may be connected to one main body.

Meanwhile, an image processor 350 that converts echo ultrasound received by the ultrasound probe 500 into an ultrasound image may be installed in the main body 100. The image processor 350 may be implemented as a hardware processor such as a microprocessor or a software processor executed on a hardware platform.

The image processor may generate an ultrasound image through scan conversion of echo ultrasound. In this regard, the ultrasound image may include not only a gray scale image acquired by scanning the object in an amplitude mode (A mode), a brightness mode (B mode), and a motion mode (M mode), but also a Doppler image representing an image of a moving object by using the Doppler Effect. The Doppler image may include a blood stream Doppler image indicating a flow of blood (color Doppler image), a tissue Doppler image showing movement of tissues, and a spectrum Doppler image illustrating a speed of a moving object as waveforms.

The image processor may extract B mode components from the echo ultrasound received by the ultrasound probe 500 to generate a B mode image.

The image processor may extract Doppler components from the echo ultrasound to generate a Doppler image in which motion of the object is expressed as color or waveforms based on the extracted Doppler components.

Furthermore, the image processor may generate a 3D ultrasound image by performing volume rendering of volume data acquired by the echo ultrasound or may generate an elastic image in which the degree of deformation of the object by pressure is imaged. In addition, the image processor may express additional information on the ultrasound image by using texts and graphics.

Meanwhile, the generated ultrasound image may be stored in an internal memory of the main body or an external memory. Alternatively, the ultrasound image may also be stored in a web storage or a cloud server.

The input unit 150 may receive an instruction related to operation of the ultrasound imaging apparatus. For example, the input unit 150 may receive an instruction to select a mode such as the A mode, the B mode, the M mode, or the Doppler image mode. The input unit 150 may also receive an instruction to initiate an ultrasound diagnosis.

The instruction input through the input unit 150 may be transmitted to the main body 100 via a wireless or wired communication network.

The input unit 150 may include at least one of a keyboard, a foot switch, and a foot pedal. The keyboard may be a hardware element located at an upper portion of the main body 100. The keyboard may include at least one of a switch, a key, a joystick, and a trackball. As another example, the keyboard may be a software element such as a graphic user interface. In this case, the keyboard may be displayed on display 160 or a sub display 170. The foot switch or foot pedal may be provided at a lower portion of the main body 100, and a user may control operation of the ultrasound imaging apparatus using the foot pedal.

The sub display 170 may be provided at the main body 100. FIG. 1 illustrates that the sub display 170 is provided on the input unit 150. The sub display 170 may display an application related to operation of the ultrasound imaging apparatus. For example, the sub display 170 may display menus, guidelines, or the like for ultrasound diagnosis. Examples of the sub display 170 may include cathode ray tubes (CRTs) and liquid crystal displays (LCDs).

The main display 160 may be provided at the main body 100. FIG. 1 illustrates that the main display 160 is provided above the sub display 170. The main display 160 may display an ultrasound image acquired during the ultrasound diagnosis in accordance with an input applied to the input unit. The main display 160 may also be a CRT or a LCD similarly to the sub display 170. Although FIG. 1 illustrates that the main display 160 is coupled to the main body 100, the main display 160 may also be separately formed from the main body 100.

FIG. 1 illustrates that the ultrasound imaging apparatus includes both the main display 160 and the sub display 170. However, the sub display 170 may not be used. In this case, applications or menus displayed on the sub display 170 may be displayed on the main display 160.

Meanwhile, the ultrasound imaging apparatus may further include a communication unit. The communication unit communicates with an external device or a server in a state of being connected in a wired or wireless network. The communication unit may transmit/receive data to/from a server of a hospital or a medical apparatus in the hospital connected via a picture archiving and communication system (PACS). In addition, the communication unit may perform data communication via the Digital Imaging and Communications in Medicine (DICOM).

The communication unit may perform transmission and reception of data related to diagnosis of the object such as an ultrasound image, echo ultrasound, and Doppler data via a network, and may also perform transmission and reception of medical images acquired by another medical apparatus such as a CT scanner, an MRI apparatus, and an X-ray apparatus. Moreover, the communication unit may receive information related to medical history or treatment schedule of a patient from the server to diagnose a disease of the object. Furthermore, the communication unit may perform data communication with a portable terminal of a doctor or a patient, in addition to the server or medical apparatus of the hospital.

The communication unit may transmit/receive data to/from a server, a medical apparatus, or a portable terminal in a wired or wireless network. The communication unit may include one or more elements enabling communications with external devices, for example, a short distance communication module, a wired communication module, and a wireless communication module.

The short distance communication module is a module for communicating with a device located within a predetermined distance. A short distance communication technology according to an exemplary embodiment may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like, without being limited thereto.

The wired communication module is a module for communicating by using an electric signal or an optical signal, and a wired communication technology according to an exemplary embodiment may be wired communication technology using a pair cable, a coaxial cable, an optical fiber cable, and an Ethernet cable.

The mobile communication module may transmit/receive a wireless signal to/from at least one of a base, an external terminal, and a server in a mobile communication network. Here, the wireless signal may be a voice call signal, a video call signal, or various types of data according to text/multimedia messages transmission.

Figure 2:
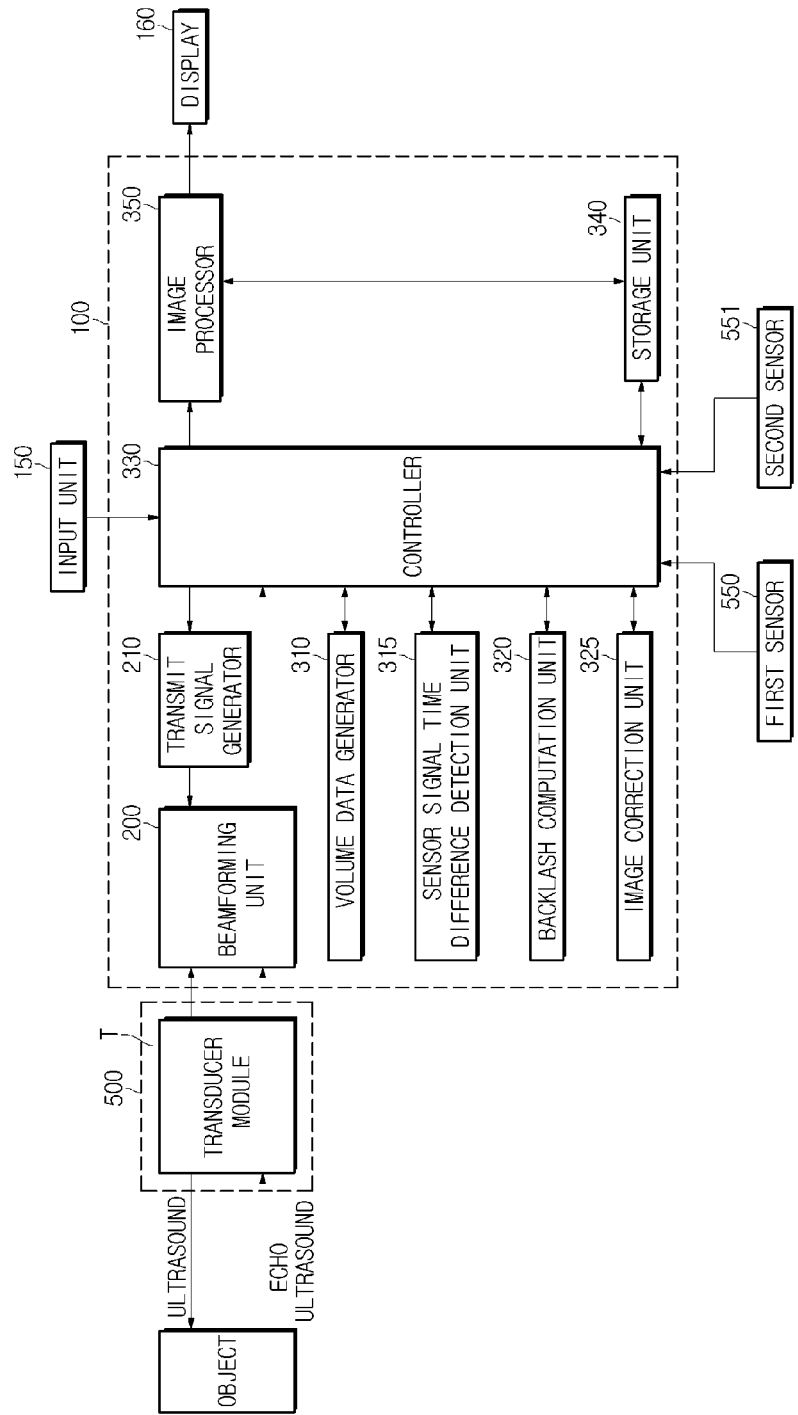
FIG. 2 is a control block diagram illustrating an ultrasound imaging apparatus according to an exemplary embodiment.

FIG. 2 is a control block diagram illustrating the ultrasound imaging apparatus.

The ultrasound probe 500 includes a plurality of transducer elements to perform interconversion between electrical signals and ultrasonic signals and may transmit ultrasonic signals to an object and receive echo signals reflected by the object. Since ultrasound reflectivity varies according to medium, the ultrasound probe 500 may acquire information regarding the inside of the object by collecting echo ultrasound.

The ultrasound probe 500 includes a transducer module T that generates ultrasound, emits the ultrasound toward a target region of the object, and receives echo ultrasound.

The transducer module T generates ultrasound in accordance with a pulse signal or alternating signal applied thereto and emits the ultrasound toward the object. The ultrasound emitted to the object is reflected by the target region of the object. The transducer module T receives reflected echo ultrasound and converts the received echo ultrasound into electric signals thereby generating ultrasonic signals.

The transducer module T receives power from an external power supply device or an internal charge storage device, such as a battery. When power is supplied, a piezoelectric vibrator or a thin film constituting the transducer module T vibrates. The transducer module T emits the ultrasound generated by vibration of the piezoelectric vibrator or the thin film to the object. When the echo ultrasound reflected by the object are received, the piezoelectric vibrator or the thin film constituting the transducer module T vibrates in accordance with the echo ultrasound. The transducer module T generates alternating current having a frequency corresponding to a vibration frequency of the piezoelectric vibrator or the thin film, thereby converting ultrasound into electric signals (hereinafter, referred to as ultrasonic signals).

Figure 3:
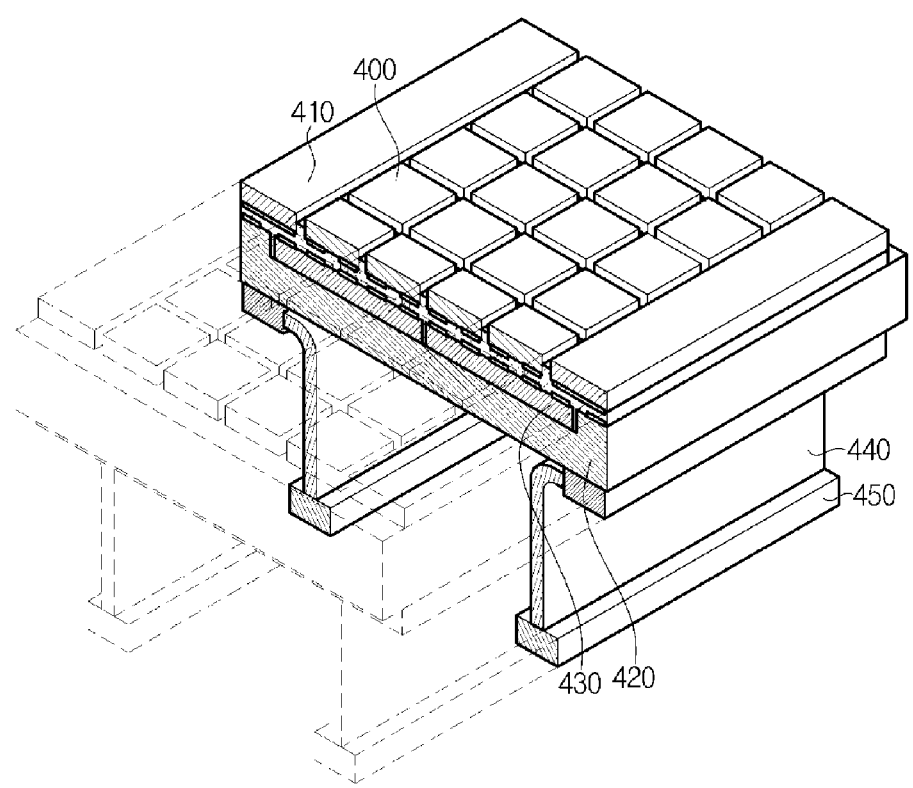
FIG. 3 is a perspective view illustrating a transducer module of an ultrasound probe.
Figure 4:
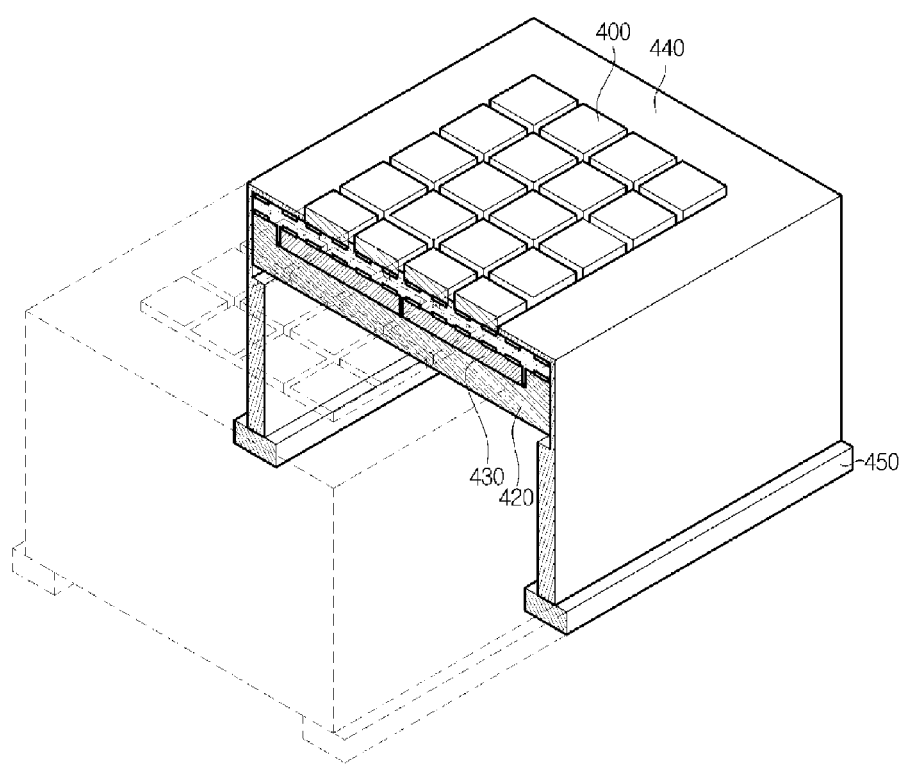
FIG. 4 is a perspective view illustrating a transducer module of an ultrasound probe.

Hereinafter, the transducer module T will be described in more detail with reference to FIGS. 3 and 4. FIGS. 3 and 4 are perspective views illustrating examples of the transducer module of the ultrasound probe.

Referring to FIG. 3, the transducer module T includes: a transducer array 400 transmitting and receiving ultrasound; a pad bridge 410 including wiring blocks for electrical connection between integrated circuits 430 and a printed circuit board 420; the integrated circuits 430 to which the transducer array 400 is bonded; the printed circuit board 420 and a flexible printed circuit board 440 connecting the integrated circuits 430 with a control board 450 to output a transmit signal output from the control board 450 to the integrated circuits 430, and the control board 450 outputting the transmit signal for generating ultrasound to the integrated circuits 430.

The transducer array 400 includes a plurality of transducer elements (not shown) that transmit and receive ultrasound. Various transducer elements such as a magnetostrictive ultrasound transducer using a magnetostrictive effect of a magnetic material widely used in ultrasound probes, a piezoelectric ultrasound transducer using a piezoelectric effect of a piezoelectric material, and a piezoelectric micromachined ultrasound transducer (pMUT) may be used. Furthermore, a capacitive micromachined ultrasound transducer (cMUT), which transmit and receive ultrasound by using vibration of hundreds or thousands of micromachined thin films may also be used.

The ultrasound probe 500 may be implemented in various ways within the technical concept of acquiring volume data of the object. For example, when the ultrasound probe 500 has one-dimensional arrangement of elements, the ultrasound probe 500 may acquire volume data in accordance with a Freehand method. Alternatively, the ultrasound probe 500 may acquire volume data by a mechanical method without having a user manipulation. When the ultrasound probe 500 has a two-dimensional arrangement of elements, the ultrasound probe 500 may acquire volume data by controlling the elements.

Particularly, when the ultrasound probe 500 receives AC power from an external power supply device or an internal power storage device such as a battery, the plurality of transducer elements vibrate to generate ultrasonic signals. The ultrasonic signals are irradiated to the object and echo signals reflected by the object are received by the plurality of transducer elements. The plurality of transducer elements vibrate in accordance with the received echo signals, thereby generating current having a frequency corresponding to vibration frequency.

Referring to FIG. 2, the main body 100 may include a transmit signal generator 210, a beamforming unit 200, a volume data generator 310, a backlash computation unit 320, a controller 330, a storage unit 340, an image processor 350.

The transmit signal generator 210 may generate a transmit signal in accordance with a control instruction from the controller 330 and transmit the generated transmit signal to the ultrasound probe 500. In this regard, the transmit signal refers to a high-voltage electric signal to vibrate the plurality of transducer elements of the ultrasound probe 500.

The beamforming unit 200, which may perform interconversion between analog signals and digital signals, converts the transmit signals (digital signals) generated by the transmit signal generator 210 into analog signals or converts echo signals (analog signals) received from the ultrasound probe 500 into digital signals allowing communication between the ultrasound probe 500 and the main body 100.

In addition, the beamforming unit 200 may apply time delays to the digital signals in consideration of positions of vibrators and a focus point to overcome time difference of arrival at the focus point among ultrasonic signals or time difference of arrival at the transducer elements from the focus point among echo signals.

That is, under an assumption that a process of concentrating ultrasonic signals, which are simultaneously emitted by the plurality of transducer elements, into a focus point is referred to as focusing, the beamforming unit 200 may perform transmit focusing, by which the ultrasonic signals respectively generated by the transducer elements are sequentially emitted in a predetermined order to remove time difference of arrival at the focus point among the ultrasonic signals, and receive focusing, by which the echo signals are simultaneously aligned at respective transducer elements by using a predetermined time difference to remove time difference of arrival at the transducer elements among the echo signals.

The beamforming unit 200 may be disposed in the main body 100 as illustrated in FIG. 2 or may be installed in the ultrasound probe 500 performing functions thereof.

The volume data generator 310 may generate a plurality of volume data before or while an external stress is applied to the object in response to a plurality of echo signals received in accordance with a plurality of ultrasonic signals transmitted by the ultrasound probe 500. In this regard, the echo signals indicate signals that are processed by various processes by a signal processing unit 332.

For example, when an echo signal received in accordance with an ultrasonic signal transmitted by the ultrasound probe 500 toward the object before an external stress is applied to the object is referred to as a first echo signal, and an echo signal received in accordance with an ultrasonic signal transmitted by the ultrasound probe 500 toward the object while the external stress is applied to the object is referred to as a second echo signal, the volume data generator 310 may generate first volume data corresponding to the first echo signal and second volume data corresponding to the second echo signal.

In this regard, the external stress may be applied to the object using a method of applying stress in a proceeding direction of ultrasound, such as a method of applying static pressure by using a hand of an examiner or the ultrasound probe 500, a method of applying high-pressure ultrasound pulse, and a method of applying mechanical vibration, or a method of applying stress in a direction perpendicular to the proceeding direction of ultrasound, such as a shearwave method using a transverse wave, without being limited thereto.

In addition, in order to three-dimensionally visualize the object, 2D cross-sectional images of the object are acquired in accordance with the echo signals received by the ultrasound probe 500, and the 2D cross-sectional images are sequentially stacked in the corresponding order thereof to generate a set of discrete 3D alignments. The set of the 3D alignments is volume data.

The main body 100 may include a sensor signal time difference detection unit 315, a backlash computation unit 320, and an image correction unit 325. These constituent elements are interlocked with the controller 330 to realize the technical concept of the present disclosure, and detailed descriptions thereof will be given later.

Figure 5:
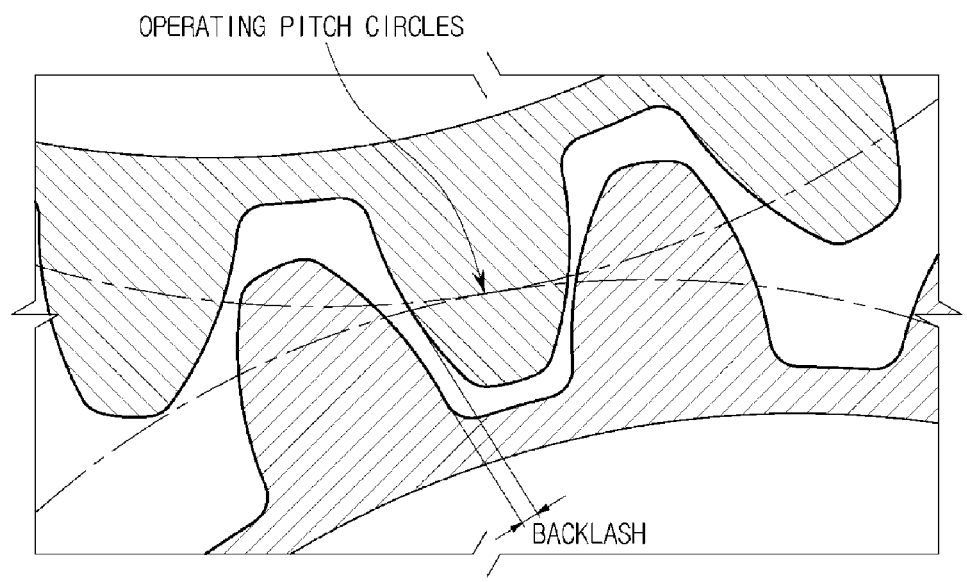
FIG. 5 is a diagram illustrating a backlash for describing causes of the backlash.

FIG. 5 is a diagram illustrating a backlash for describing causes of the backlash.

Referring to FIG. 5, the backlash refers to a gap between a pair of gears required to smoothly rotate the gears. For smooth rotation of a gear train in an engaged state, an upper gear and a lower gear need to be engaged with each other with a predetermined gap as illustrated in FIG. 5. In this case, when the backlash is too small, a gap between the gears is insufficient for smooth rotation of the gears in the engaged state, and thus friction between the gears increases due to insufficient lubrication, causing a breakdown or malfunctioning of the gears. On the other hand, as the backlash is too large, teeth of the gears cannot be sequentially engaged with each other and the gears may deviate from the original operating state thereof. Thus, although an appropriate backlash is required for smooth rotation of the gears, an operation error of the gears occurs when the backlash changes from an initial state. Thus, this phenomenon needs to be prevented. The backlash and burring of an image will be described in detail later with reference to (c) of FIG. 7.

Figure 6:
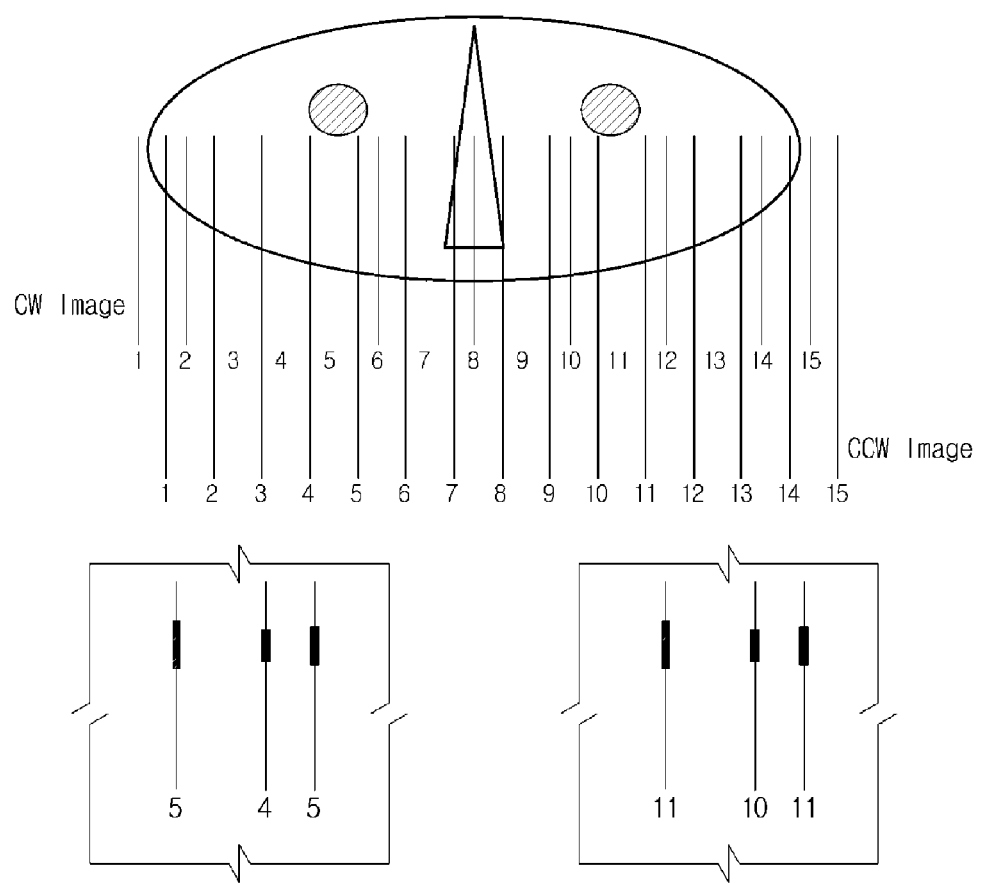
FIG. 6 is a diagram illustrating scanning of a face by using a conventional linear ultrasound probe.

FIG. 6 is a diagram illustrating scanning of a face by using a conventional linear ultrasound probe.

As illustrated in FIG. 6, when a conventional linear ultrasound probe is used, a clockwise image is different from a counter clockwise image. More particularly, while one image (thin solid line 5 or 11) is acquired for each eye marked by diagonal lines as the clockwise image, two images (thick solid lines 4 and 5 or 10 and 11) are acquired for each eye as the counter clockwise image. Thus, a mismatch occurring between the two images while compounding the images may cause blurring of an ultrasound image.

Figure 7:
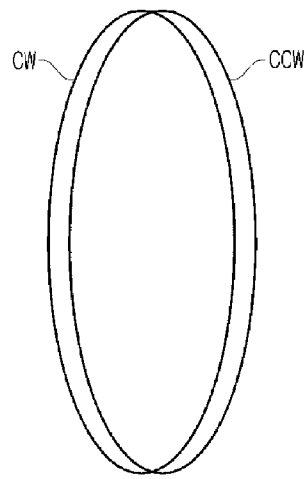
FIG. 7 is a diagram illustrating blurring of an ultrasound image caused by a backlash and an ultrasound image in which the blurring is removed by image correction using an ultrasound probe and a method of controlling the same according to an exemplary embodiment.
Figure 7:
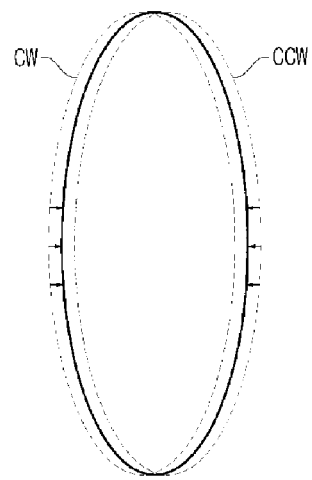
Figure 7:
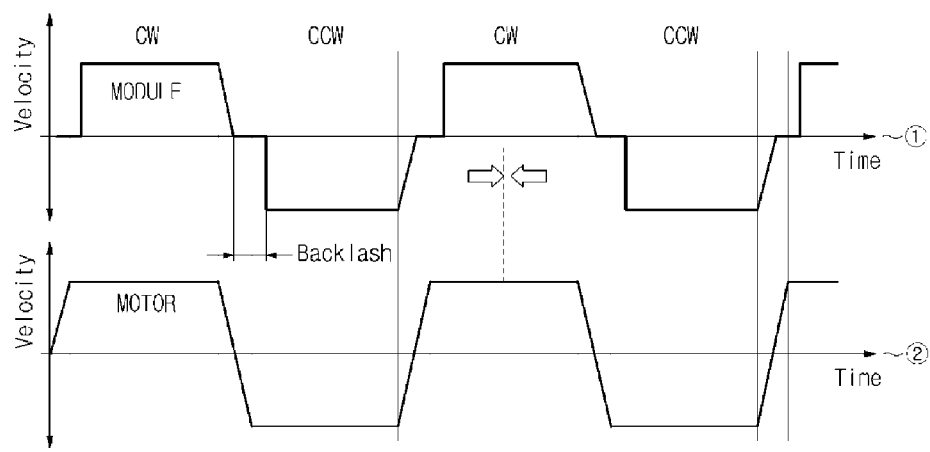

FIG. 7 illustrates blurring of an ultrasound image caused by a backlash and an ultrasound image in which the blurring is removed by image correction using an ultrasound probe and a method of controlling the same according to an exemplary embodiment.

(A) of FIG. 7 is a diagram for describing blurring of an image caused by an ultrasound probe, and (c) of FIG. 7 is a diagram for describing a backlash as a cause of blurring of the image.

As illustrated in (a) of FIG. 7, when a transducer array of an ultrasound probe laterally wobbles, an initial ultrasound image is acquired by compounding a clockwise image CW received clockwise and a counter clockwise image CCW received counter clockwise. In this regard, velocity of ultrasound transmitted clockwise or counter clockwise is delayed, and the received two images cannot overlap each other appropriately, causing blurring of the image. That is, in (a) of FIG. 7, a left circle is an image received clockwise, and a right circle is an image received counter clockwise. The two images cannot overlap each other, thereby causing blurring of the ultrasound image.

Such blurring of the image is caused by a backlash which will be described in more detail with reference to FIG. 5. Backlash occurring in the ultrasound probe refers to a delay of rotational motion of a motor, which is a driving device, when the rotational motion is transferred to a transducer, and the backlash is a parameter moving the motor prior to an effective zone signal. The backlash is calculated as an error between a theoretical change in an angle of an alignment axis of an ultrasound transmitting and receiving device in accordance with a change in an angle of the motor (driving shaft) and an actual change in the angle of the alignment axis. The backlash is used to evaluate the degree of maintaining an initial error as the number of driving increases.

The backlash may be classified into backlash caused by a processing tolerance and assembly tolerance of an apparatus and backlash caused by abrasion, or the like, as the number of driving increase. The former is referred to as constant backlash, and the latter is referred to as delta backlash. The constant backlash is constantly maintained as compared with backlash measured during the early stage even when the number of driving increases. The backlash used in the ultrasound probe and the method of controlling the same according to an exemplary embodiment is delta backlash.

Graph ① of (c) of FIG. 7 is a velocity-time graph of the transducer module with respect to rotation, and graph ② of (c) of FIG. 7 is a velocity-time graph of the motor of the driving device with respect to rotation.

A driving device 520 of the ultrasound probe 500, which will be described later with reference to FIG. 8B, may include a driving motor 521 to generate a rotational force therein and a driving shaft 522 to receive a power from the driving motor 521 to rotate a transducer 510.

As the driving motor 521 rotates, the transducer 510 rotates in the same direction. In this case, when the transducer 510 does not rotate in accordance with the rotation of the driving motor 521, a delay occurs. Upon comparison between graph ① and graph ②, when rotation of the driving motor 521 is changed from clockwise CW to counter clockwise CCW, the transducer 510 cannot rotate in accordance therewith causing a delay as illustrated in graph ②. Accordingly, backlash occurs by a delayed gap. As illustrated in a portion marked by dashed lines, alignment axes (central axes) of the driving motor 521 and the transducer 510 are not the same as initial axes thereof, and thus the clockwise image and the counter clockwise image do not match with each other, thereby causing blurring of the image.

As illustrated in (b) of FIG. 7, the blurring of the image is corrected via image correction according to an exemplary embodiment by shifting the mismatched clockwise image CW and the counter clockwise image CCW by the delay caused by the backlash with respect to the central axis. That is, the blurring is removed by matching the clockwise image CW and the counter clockwise image CCW. The ultrasound probe and correction of the blurring of the image according to the method of controlling the ultrasound probe according to an exemplary embodiment will be described in more detail.

Figure 8A:
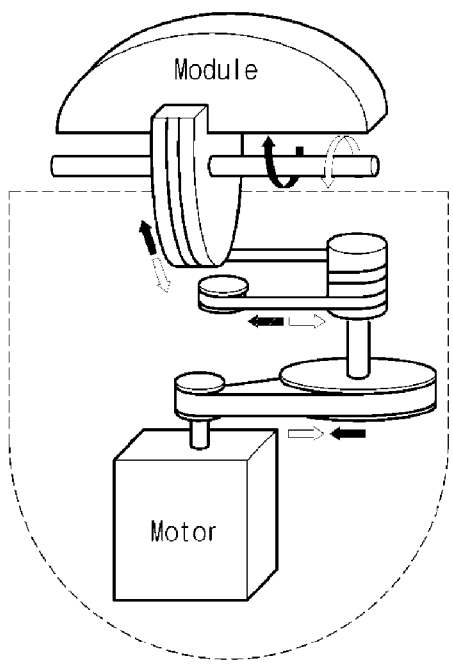
FIG. 8A is a diagram schematically illustrating operation of a 3D ultrasound probe according to an exemplary embodiment.
Figure 8A:
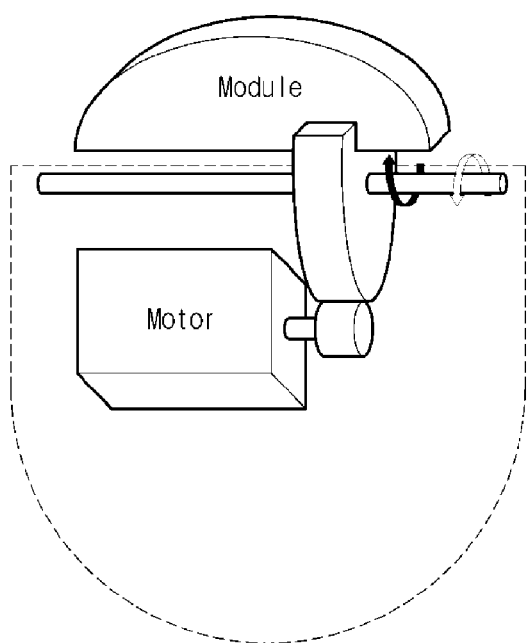

FIG. 8A is a diagram schematically illustrating operation of a 3D ultrasound probe.

Among ultrasound probes, a 3D ultrasound probe will be exemplarily described according to an exemplary embodiment.

As illustrated in FIG. 8A, in a 3D ultrasound probe, a transducer (module) rotates by rotation of a driving motor. A rotational force of the driving motor may be transferred to the transducer via a separate rotation shaft or rotation gear disposed between a rotation shaft of the driving motor and a rotation shaft of the transducer as illustrated in (a) of FIG. 8A. Alternatively, the rotational force of the driving motor may be transferred to the transducer by directly engaging a gear of the driving motor with a rotation shaft of the transducer as illustrated in (b) of FIG. 8A. When the transducer does not rotate in accordance with the rotation of the driving motor, a delay is caused due to backlash. Thus, blurring of the image may be caused by the backlash between rotation of the driving motor and rotation of the transducer. The 3D ultrasound probe will be described in more detail with reference to FIG. 8B.

Figure 8B:
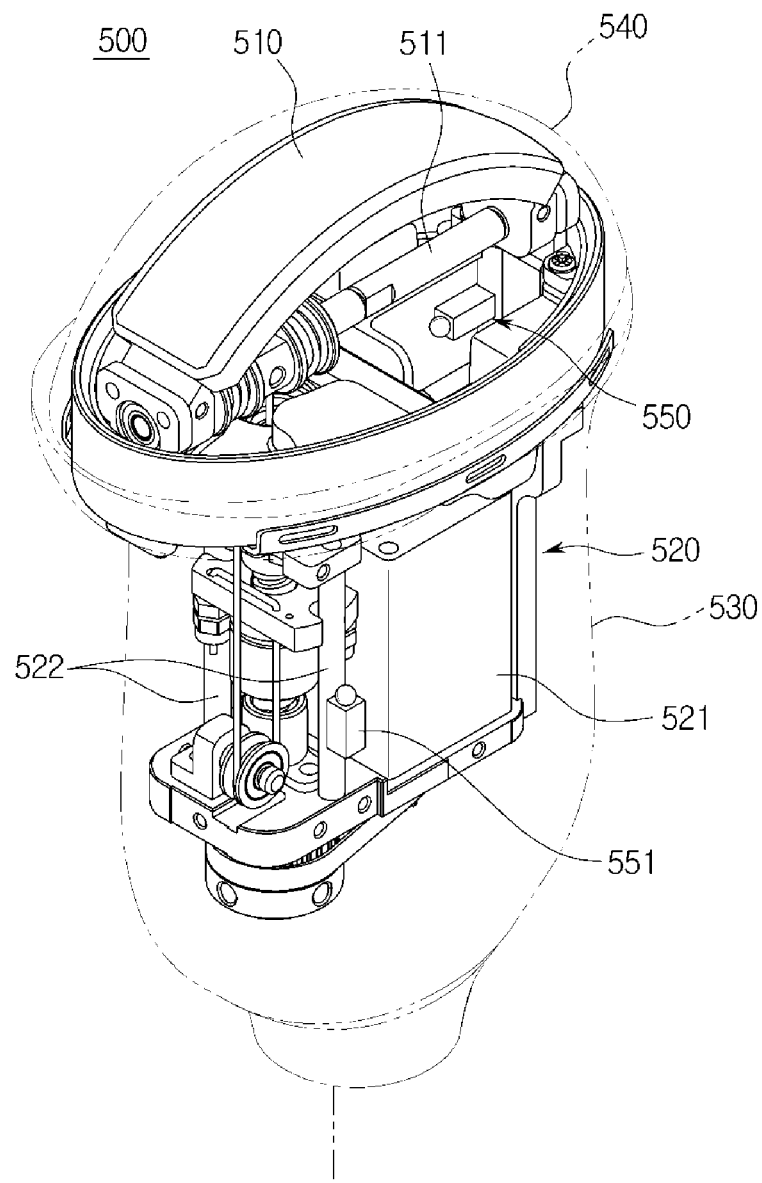
FIG. 8B is a perspective view illustrating an inner structure of an ultrasound probe according to an exemplary embodiment.

FIG. 8B is a perspective view illustrating an inner structure of the ultrasound probe 500.

The ultrasound probe 500 includes a transducer 510 rotatably installed, a driving device 520 generating power to rotate the transducer 510, a handle case 530 accommodating the driving device 520 therein and gripped by a user for use of the ultrasound probe 500, and a cap 540 accommodating the transducer 510 therein.

The transducer 510 includes ultrasound vibrators that transmit and receive ultrasound and is rotatably installed inside the cap 540 as described above to acquire a 3D image of an object to be diagnosed. The transducer 510 includes a shaft 511 constituting the rotation center thereof, and both ends of the shaft 511 may be rotatably installed and may be rotate about the shaft 511.

The driving device 520 is fixed to an inner portion of the handle case 530.

The driving device 520 may include the driving motor 521 to generate an inner rotational force, and the driving shaft 522 to receive power from the driving motor 521 and rotate the transducer 510.

The cap 540 may have a cross-section with an arc-shaped portion corresponding to a rotating portion of the transducer 510 such that a distance between an inner surface of the cap 540 and an outer surface of the transducer 510 is constantly maintained even when the transducer 510 installed therein rotates.

An inner space of the cap 540 may be filled with an oil serving as a medium for transmitting ultrasound generated by the transducer 510. Functions and characteristics of the cap 540 will be described later.

Hereinafter, an aqueous solution substituting for the oil filled in the inner space of the cap 540 will be described with reference to FIG. 9.

Figure 9:
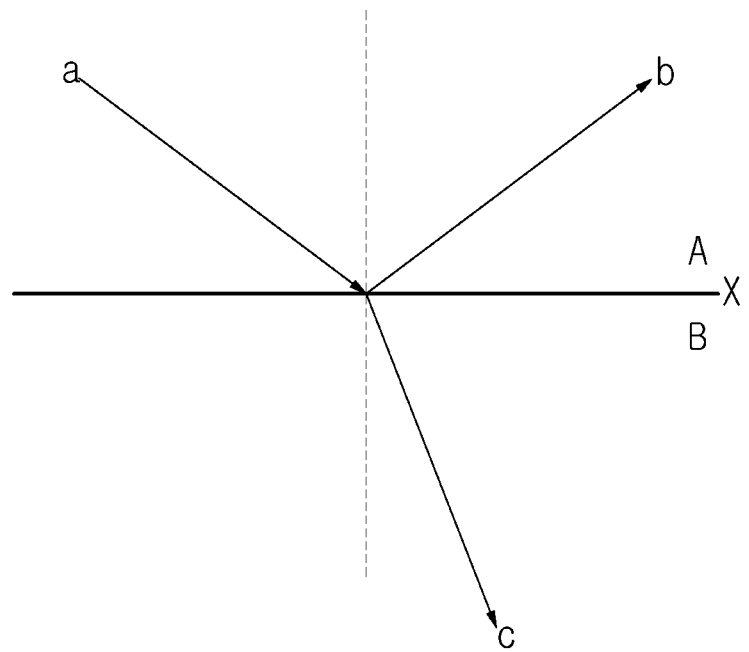
FIG. 9 is a diagram illustrating that light travels from one medium to another.

FIG. 9 is a diagram illustrating that light travels from one medium to another.

A refers to medium A, B refers to medium B, and X refers to a contact surface between the medium A and B. In addition, a refers to an incident ultrasound, b refers to a reflected ultrasound, and c refers to a refracted ultrasound. A dashed line is perpendicular to X.

Ultrasound diagnosis is a process of examining a contour or shape of an object by measuring intensity of ultrasound reflected by the object. Ultrasound is reflected by a boundary between medium, i.e., a boundary where an acoustic impedance is changed. Thus, since intensity of ultrasound is changed according to acoustic impedance, which is an intrinsic value of a material, a change of the medium in the object may be identified by the ultrasound diagnosis by using these properties.

Referring to FIG. 9, an ultrasound is reflected by the contact surface X between the medium A and the medium B. In order to examine inner tissues, an amount of the reflected ultrasound needs to be minimized. Thus, a difference of acoustic impedance between the medium A and B needs to be minimized.

To this end, impedance matching is required. That is, reflection of ultrasound may be reduced by decreasing the difference of acoustic impedance with skin tissues. In this case, an oil for ultrasound diagnosis having an acoustic impedance similar to that of the human body, i.e., 1.63 MRayl, is used. When the oil having the acoustic impedance similar to the human body is applied between the ultrasound probe and the skin filling an air layer therebetween, reflection of ultrasound by the air layer may be reduced. Since the amount of ultrasound reaching the target region in the object increases, more accurate information may be acquired.

The oil needs to have high transmissivity in addition to the acoustic impedance condition. Also, the oil needs to have very low absorptivity, high viscosity sufficient for continuously staying on the skin during the treatment, and high lubricating quality such that the ultrasound probe smoothly moves in a contact with the skin, without causing skin irritation.

As illustrated in FIG. 8B, the ultrasound probe 500 according to an exemplary embodiment is provided with a first sensor 550 configured to detect a position of the transducer 510 changed by rotation, and a second sensor 551 configured to detect rotation of the driving device 520. Appearances of the first sensor 550 and the second sensor 551 are illustrated in FIG. 10.

Figure 10:
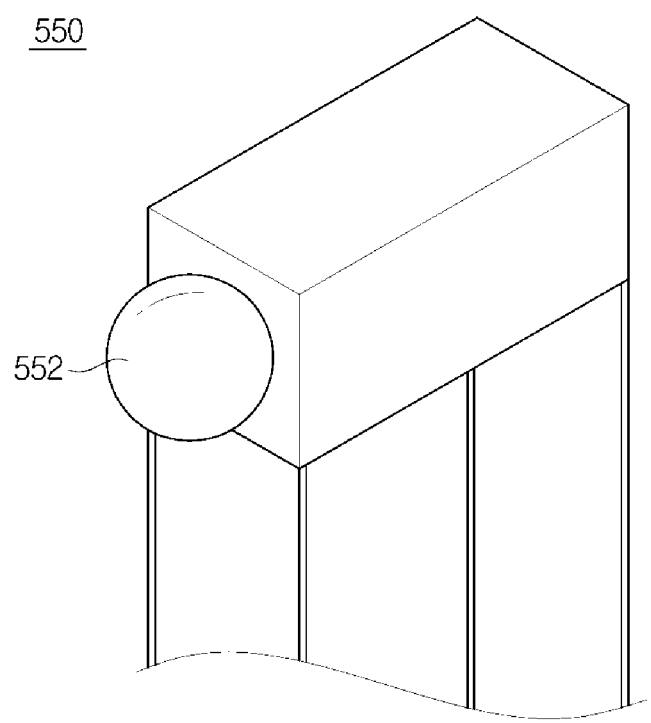
FIG. 10 is a perspective view illustrating an appearance of a first sensor.

FIG. 10 is a perspective view of the first sensor 550, and the second sensor 551 has the same appearance as the first sensor 550.

As illustrated in FIG. 10, each of the first sensor 550 and the second sensor 551 includes a position recognition unit 552 configured to detect a position of the transducer 510 changed by rotation and rotation of the driving device 520. The first sensor 550 or second sensor 551 may be connected to the controller 330 of the ultrasound imaging apparatus by circuit wiring.

More particularly, the first sensor 550 may be mounted on a position adjacent to the transducer 510 disposed in the transducer module including the transducer 510 of the ultrasound probe or may directly be mounted on the transducer 510. Since the first sensor 550 detects the position of the transducer 510 changed by rotation, the mounting position thereof is not limited.

The second sensor 551 may be mounted on the driving device 520 disposed in the ultrasound probe. More particularly, the driving device 520 includes a driving motor 521 generating a rotational force to rotate the transducer 510 and a driving shaft 522 transferring the rotational force of the driving motor 521 to the transducer 510. As the driving motor 521 operates, the driving shaft 522 rotates, and the transducer 510 rotates to operate the ultrasound probe 500 such that a rotation direction of the driving motor 521 is identical to a rotation direction of the transducer 510. The second sensor 551 senses the rotation of the driving device 520, i.e., the driving motor 521, detects a signal, and compares the detected signal with a signal detected by the first sensor 550. Thus, the second sensor 551 may be mounted on the driving shaft 522 or may be implemented as a device sensing the rotation of the driving motor 521 and outputting a signal in the driving motor 521. Since the second sensor 551 detects rotation of the driving motor 521 included in the driving device 520, the position thereof is not limited. Operations of the first sensor 550 and the second sensor 551, a process of calculating backlash based on signals output as a result of the position detection, and a process of correcting an ultrasound image based on the backlash will be described in detail later with reference to FIGS. 11 and 12.

Figure 11:
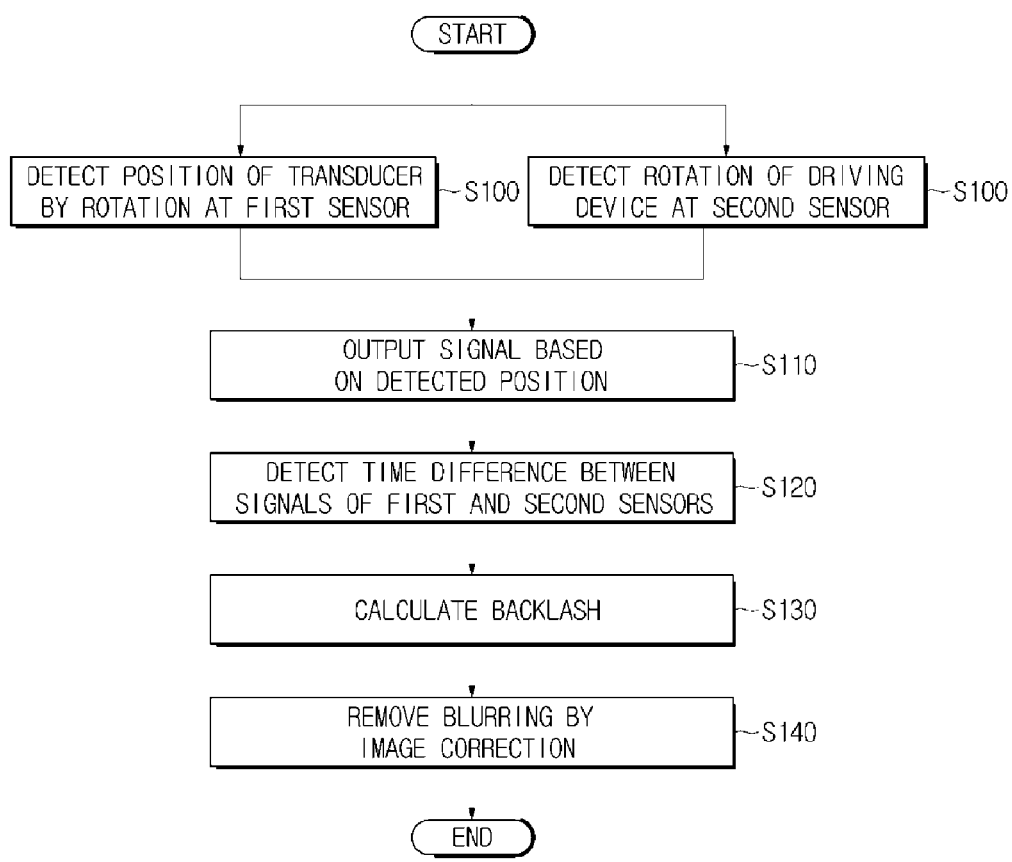
FIG. 11 is a flowchart illustrating a method of controlling an ultrasound probe according to an exemplary embodiment.

FIG. 11 is a flowchart illustrating a method of controlling an ultrasound probe according to an exemplary embodiment.

Referring to FIG. 11, the method of controlling an ultrasound probe according to an exemplary embodiment includes detecting a position of a transducer changed by rotation at a first sensor and detecting a rotation of a driving device at a second sensor (S100), outputting a signal based on the detected position (S110), detecting a time difference between signals from the first sensor and the second sensor (S120), calculating a backlash (S130), and removing blurring of an image by correcting the image (S140).

Figure 12:
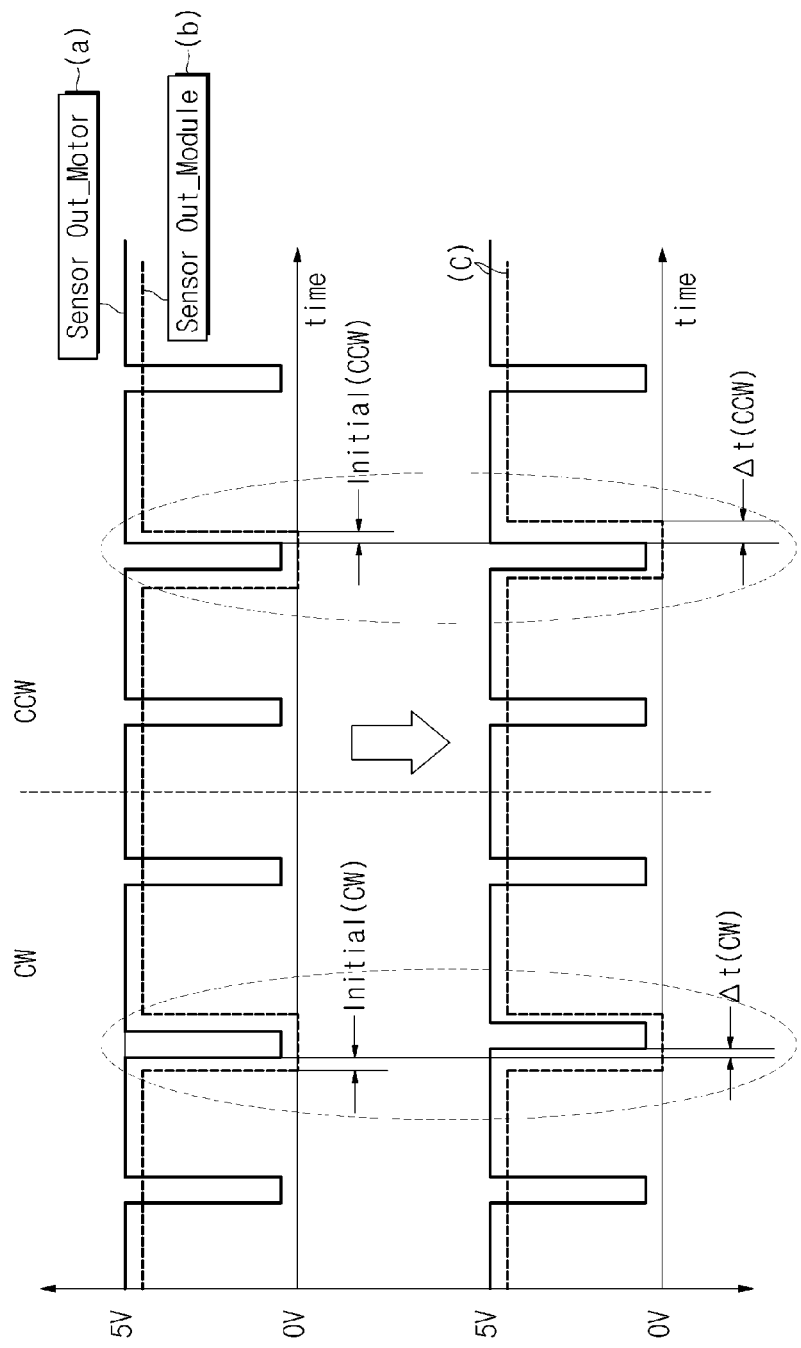
FIG. 12 is a graph illustrating signals output from a first sensor and signals output from a second sensor with respect to time according to a method of controlling an ultrasound probe according to an exemplary embodiment.

More particularly, the first sensor 550 mounted on a position adjacent to the transducer 510 detects a position of the transducer 510 changed by rotation when the transducer 510 rotates clockwise and counter clockwise and outputs the detected position as a signal. As illustrated in FIG. 10, the position recognition unit 552 of the first sensor 550 detects the position of the transducer 510 in real time and outputs the signal. The signal is output in the form as illustrated in FIG. 12.

The driving motor 521 of the driving device 520 of the ultrasound probe 500 is set to rotate at a constant velocity v when a driving command is received from the controller 330. The rotation velocity of the driving motor 521 may vary according to a setting value input to a motor board (not shown) disposed in the driving motor 521, and the signal is output in accordance with velocity v, distance s, and time t of the driving motor 521. That is, as the driving motor 521, the velocity of which is set, rotates, a power is transferred via the driving shaft 522 to rotate the transducer 510. A time period t during which the transducer 510 rotates at a predetermined velocity v by a predetermined distance s is detected, and the detected time period t is illustrated as a waveform with respect to the signal as illustrated in FIG. 12.

The second sensor 551 is mounted on the driving shaft 522 of the driving device 520. Since a rotational power generated as the driving motor 521 of the driving device 520 rotates is transferred to the transducer 510 via the driving shaft 522, the second sensor 551 may be mounted on the driving shaft 522 of the driving device 520 to detect a delay caused by rotation of the driving motor 521 and the transducer 510 and to detect a backlash. Since the driving motor 521 may directly detect rotation of the driving motor 521, the position of the second sensor 551 or sensing of the rotation of the driving motor 521 is not limited. The process of sensing rotation of the driving device 520 and outputting the detection as a signal performed at the second sensor 551 is the same as that performed at the first sensor 550, and thus detailed descriptions thereof will not be given.

As described above, the first sensor 550 detects a position of the transducer 510 changed by rotation (S100), the second sensor 551 detects rotation of the driving device 520 (S100), and a signal with regard to the time period t as described above is output (S110).

FIG. 12 is a graph illustrating signals from a first sensor and signals from a second sensor with respect to time according to a method of controlling an ultrasound probe according to an exemplary embodiment.

When the first sensor 550 and the second sensor 551 output signals as illustrated in FIG. 12, circuit wiring from the first sensor 550 and the second sensor 551 to the controller 330 may vary. Since a conventional ultrasound probe does not include a plurality of sensors to detect a position of the ultrasound probe, 3 circuit wirings are used. However, since the ultrasound probe 500 according to an exemplary embodiment includes a plurality of sensors mounted on the transducer 510 and the driving motor 521 to detect signals, 4 circuit wirings including circuit wirings connected from each of the first sensor 550 and the second sensor 551 may be used. In this case, a time difference between a signal from the first sensor 550 and a signal from the second sensor 551 may be directly calculated.

In addition, in the circuit wiring, a signal acquired by directly calculating a difference between the signal from the first sensor 550 and the signal from the second sensor 551 by using a logic circuit such as an AND gate may be output. In this case, 3 circuit wirings may be used in the same manner as the conventional method. That is, various circuit wirings may be used.

Referring to FIG. 12, graph (a) shows a signal output from the second sensor 551 and acquired by detecting the rotation of the driving motor 521, graph (b) shows a signal output from the first sensor 550 and acquired by detecting the position of the transducer 510 changed by rotation. The signals illustrated in FIG. 12 may be referred to as Null signals, without being limited thereto.

Referring to FIG. 12, the transducer 510 and the driving motor 521 repeat clockwise CW rotation about the central axis and counter clockwise CCW rotation. In graph (b), a time when the signal is 0 [V] is a time when the rotation of the transducer 510 temporarily stops, and a position where graph (a) and graph (b) overlap each other at 0 [V] corresponds to the central axis of the transducer 510. That is, referring to graph (b), a switchover time from the clockwise CW rotation to the counter clockwise CCW rotation after the transducer 510 initiates the clockwise CW rotation about the central axis corresponds to the central line of the graph. Thus, after the switchover time, the transducer 510 is located at the central axis after the counter clockwise CCW rotation. Here, the signal output from the transducer 510 overlaps the signal from the driving motor 521 at 0 [V].

As illustrated in FIG. 12, an Initial (CW) value indicates a difference between a position of the driving motor 521 and a position of the transducer 510 by the clockwise rotation during the early stage as time, and an Initial (CCW) value indicates a difference between a position of the driving motor 521 and a position of the transducer 510 by the counter clockwise rotation during the early stage as time. The Initial (CW) value and the Initial (CCW) value are defaults of the ultrasound probe 500.

Graph (c) of FIG. 12 illustrates signals output to calculate a backlash caused as the ultrasound probe 500 is used. Δt(CW) is a time difference variation between signals from the first sensor 550 and the second sensor 551, as a value indicating a delay of rotation of the transducer 510 in comparison with the Initial (CW) value. That is, in case of the CW rotation, since the rotation of the transducer 510 cannot catch up the rotation of the driving motor 521, a delay occurs from the Initial(CW) value by Δt(CW). In case of the CWW rotation, a delay further occurs in the CCW direction, Δt(CCW) is greater than Δt(rCW).

The flowchart of FIG. 11 will be described with reference to FIGS. 2 and 12. When the first sensor 550 and the second sensor 551 detect positions of the transducer 510 and the driving device 520 changed by rotation and output signals (S110), the sensor signal time difference detection unit 315 detects a time difference between the signal from the first sensor 550 and the signal from the second sensor 551 (S120). As illustrated in FIG. 12, under controlling by the controller 330, an interval between the signal from the first sensor 550 and the signal from the second sensor 551 is detected, and a delayed time of the transducer 510 with respect to the rotation of the driving motor 521 is determined.

The backlash computation unit 320 calculates a backlash between the transducer 510 and the driving motor 521 in an interlocked manner with the controller 330 (S130). The backlash is calculated by calculating variations Δt(CW) and Δt(CCW) by using a time difference between signals detected by the sensor signal time difference detection unit 315 and initial time differences Initial(CW) and Initial (CCW).

The image correction unit 325 corrects the ultrasound image by using the calculated backlash to remove the blurring of the ultrasound image (S140). Particularly, since the calculated backlash is represented by a unit of time t, a delayed distance of the transducer 510 by the backlash, i.e., an increased angle, may be determined by using the backlash and velocity v of the driving motor 521. The controller 330 controls the image correction unit 325 to correct the ultrasound image at a time when the ultrasound image is rendered by the delayed value.

A method of rendering an image by using a clockwise ultrasound image and a counter clockwise ultrasound image will be briefly described. For example, one 3D image is generated by aligning 50 pieces of clockwise cross-sectional images, and one 3D image is generated by aligning 50 pieces of counter clockwise cross-sectional images. Then, the two 3D images are compounded into one image.

In this case, the image correction unit 325 may output an image from which blurring is removed, by shifting a clockwise image and the counter clockwise image delayed by the backlash by the delay ((b) of FIG. 7). That is, the image is corrected by offsetting the amount of blurring caused by the backlash. The correction of the image may be performed at any time by using the backlash calculated in real time or at regular periods or time intervals. By correcting the clockwise and counter clockwise images by the backlash, an ultrasound image from which blurring is removed may be output.

Figure 13A:
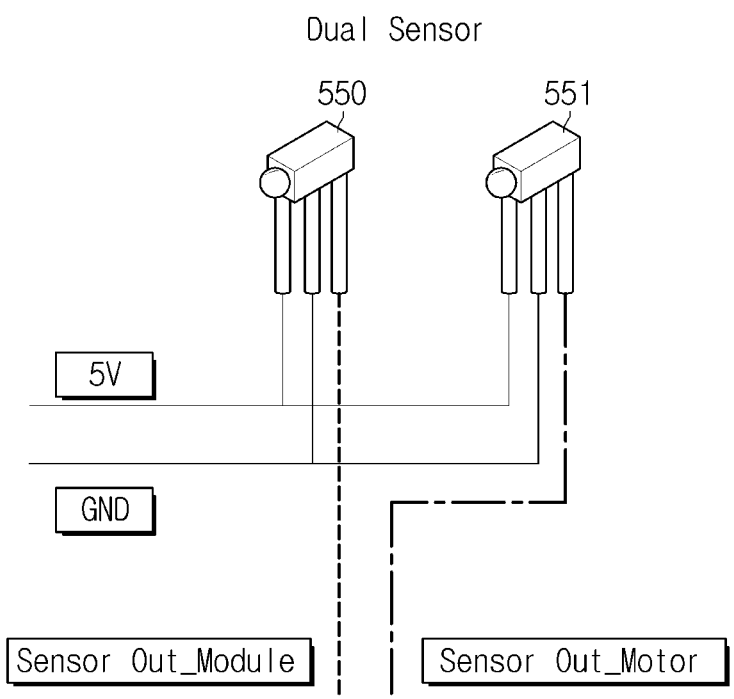
FIGS. 13A and 13B are examples of changing circuit wirings from a first sensor and a second sensor to a controller to output signals from the first sensor and the second sensor.
Figure 13A:
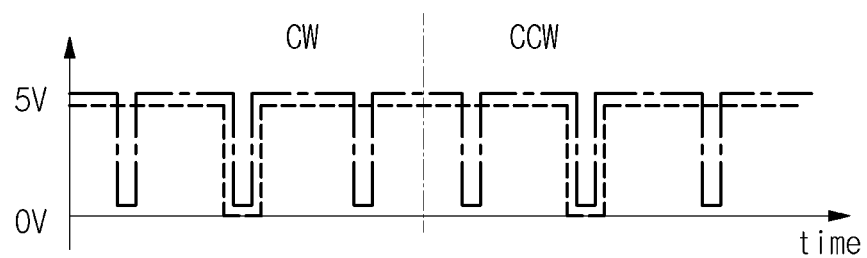
Figure 13B:
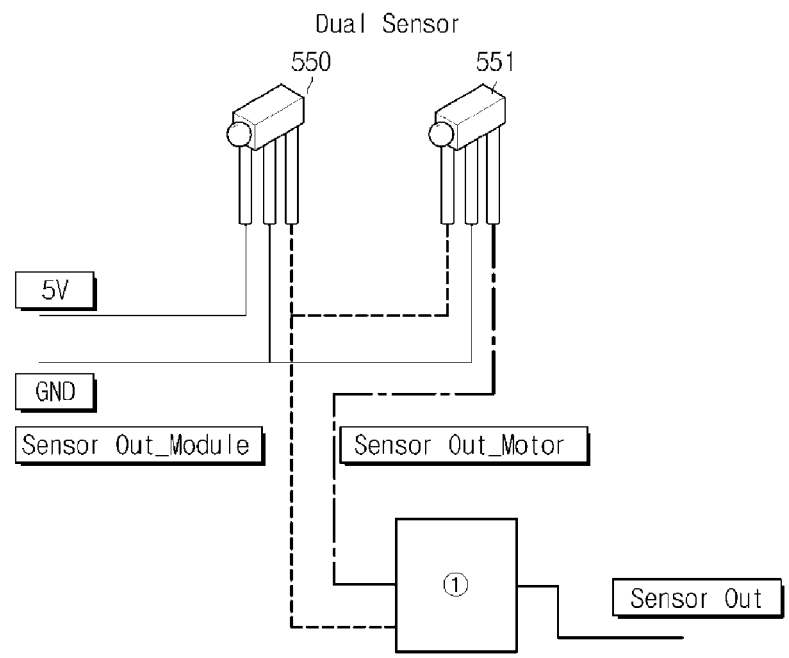
Figure 13B:
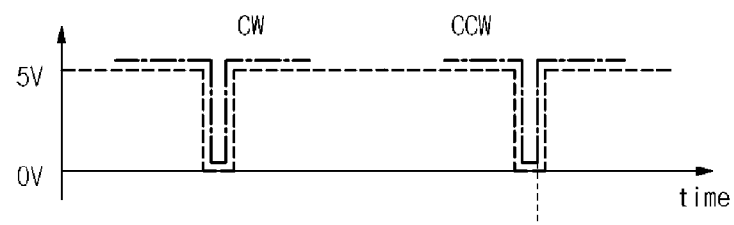
Figure 13B:
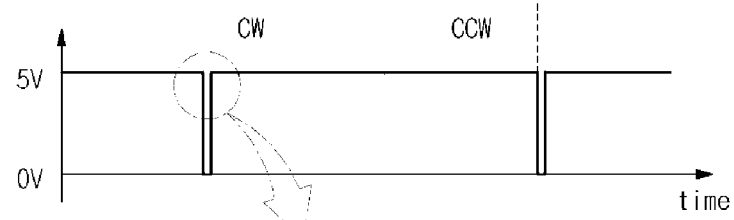
Figure 13B:
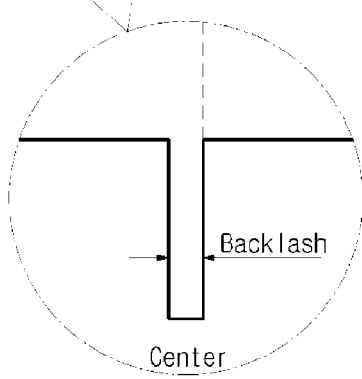

FIGS. 13A and 13B are examples of changing circuit wirings from the first sensor 550 and the second sensor 551 to the controller 330 to output signals from the first sensor 550 and the second sensor 551.

As illustrated in FIG. 13A, the ultrasound probe 500 according to an exemplary embodiment detects signals by mounting the first sensor 550 and the second sensor 551 on the driving motor 521 and the transducer 510 and may use 4 circuit wirings including wirings from each other first sensor 550 and the second sensor 551. In this case, the backlash may be calculated by calculating the difference between the signals output from the first sensor 550 and the second sensor 551.

In addition, as illustrated in FIG. 13B, the ultrasound probe 500 may output a backlash calculated by directly calculating a difference between the signal output from the first sensor 550 and the signal output from the second sensor 551 by passing the circuit wirings from the first sensor 550 and the second sensor 551 through a separate logic circuit. FIG. 13B illustrates a logic circuit ①, and a lower graph illustrates a method of directly expressing the backlash by using the logic circuit ①.

The ultrasound probe capable of correcting blurring of an ultrasound image by calculating a backlash and a method of controlling the same are described above.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound probe comprising a transducer array configured to generate ultrasound and a driving device configured to rotate the transducer, the ultrasound probe comprising:
  a first sensor configured to detect a position of the transducer changed by rotation;

a second sensor configured to detect rotation of the driving device; and a controller configured to determine a backlash value between a signal of the first sensor and a signal of the second sensor and correct an ultrasound image.

2. The ultrasound probe according to claim 1, wherein the driving device comprises:

a driving motor configured to generate a rotational force to rotate the transducer; and a driving shaft configured to transfer the rotational force of the driving motor to the transducer.

3. The ultrasound probe according to claim 1, wherein the first sensor and the second sensor are installed in the ultrasound probe.

4. The ultrasound probe according to claim 1, wherein the controller calculates a time difference variation between a signal of the first sensor and a signal of the second sensor and determines the backlash value by using the calculated time difference variation.

5. The ultrasound probe according to claim 4, wherein the controller calculates a time difference between a signal of the first sensor and a signal of the second sensor when the transducer rotates clockwise or counter clockwise.

6. The ultrasound probe according to claim 4, wherein the controller determines the backlash value by using a variation based on the detected time difference between the signal of the first sensor and the signal of the second sensor and an initial time difference.

7. The ultrasound probe according to claim 1, wherein the controller corrects a rendered clockwise image and a rendered counter clockwise image by using the determined backlash value when a rendered ultrasound image is generated.

8. The ultrasound probe according to claim 7, wherein the controller shifts the clockwise image and the counter clockwise image by the calculated backlash value of the clockwise direction and the counter clockwise direction with respect to a central axis of the transducer.

9. A method of controlling an ultrasound probe comprising a transducer array configured to generate ultrasound and a driving device configured to rotate the transducer array, the method comprising:

determining a backlash value between a signal of a first sensor and a signal of a second sensor installed in the ultrasound probe; and correcting an ultrasound image by using the determined backlash value.

10. The method according to claim 9, wherein the signal of the first sensor is a signal output as a result of detecting a position of the transducer changed by rotation.

11. The method according to claim 9, wherein the signal of the second sensor is a signal output as a result of detecting rotation of the driving device.

12. The method according to claim 9, wherein the determining of the backlash value between the signal of the first sensor and the signal of the second sensor is performed by calculating a time difference variation between the signal of the first sensor and the signal of the second sensor, and determining the backlash value by using the calculated time difference variation.

13. The method according to claim 12, wherein the calculating of the time difference between the signal of the first sensor and the signal of the second sensor is performed by calculating a time difference between the signal of the first sensor and the signal of the second sensor when the transducer rotates clockwise or counter clockwise.

14. The method according to claim 12, wherein the determining of the backlash value is performed by using a variation based on the detected time difference between the signal of the first sensor and the signal of the second sensor and an initial time difference.

15. The method according to claim 9, wherein the correcting of the ultrasound image is performed by correcting a rendered clockwise image and a rendered counter clockwise image by using the determined backlash value when a rendered ultrasound image is generated.

16. The method according to claim 15, wherein the correcting of the ultrasound image is performed by shifting the clockwise image and the counter clockwise image by the calculated backlash value of the clockwise direction and the counter clockwise direction with respect to a central axis of the transducer.

* * * * *